United States Patent [19]

Berényi neé Poldermann et al.

[11] 4,342,766
[45] Aug. 3, 1982

[54] NOVEL DIHYDRO-AS-TRIAZINO[5,6-c]QUINOLINE DERIVATIVES AND A PROCESS FOR THE PREPARATION THEREOF

[75] Inventors: Edit Berényi neé Poldermann; Péter Görög; Katalin Grasser; Ibolya Kosóczky; Ágnes Korács neé Palotay; Lujza Petöcz, all of Budapest, Hungary

[73] Assignee: Egyt Gyogyszervegyeszeti Gyar, Budapest, Hungary

[21] Appl. No.: 254,763

[22] Filed: Apr. 16, 1981

[30] Foreign Application Priority Data

Apr. 18, 1980 [HU] Hungary ............................... 939

[51] Int. Cl.³ ................. C07D 471/04; A61K 31/395
[52] U.S. Cl. ..................................... 424/249; 544/184
[58] Field of Search ......................... 544/184; 424/249

[56] References Cited

U.S. PATENT DOCUMENTS

| | | | |
|---|---|---|---|
| 3,721,670 | 3/1973 | Wright et al. ............... | 544/184 |
| 3,873,541 | 3/1975 | Berenyi et al. ............ | 544/184 |
| 3,873,542 | 3/1975 | Berenyi et al. ............ | 544/184 |
| 3,873,543 | 3/1975 | Berenyi et al. ............ | 544/184 |

FOREIGN PATENT DOCUMENTS 1382781  2/1975  United Kingdom ............... 544/184

Primary Examiner—John M. Ford
Attorney, Agent, or Firm—Karl F. Ross

[57] ABSTRACT

New compounds are disclosed of the formulae

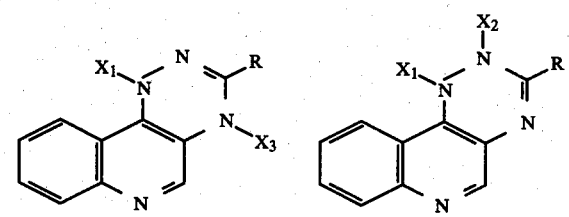

or pharmaceutically effective salts thereof, wherein
R is hydrogen, $C_{1-12}$ alkyl, or R is phenyl or phenyl-$C_1$ to $C_4$ alkyl wherein the phenyl can be substituted with 1 to 3 halogen, $C_1$ to $C_4$ alkyl, or $C_1$ to $C_4$ alkoxy substituents; and
$X_1$, $X_2$ and $X_3$ are hydrogen, $C_1$ to $C_6$ alkanoyl, or $C_1$ to $C_6$ haloalkanoyl; and where $X_1$ is hydrogen, $X_2$ and $X_3$ are not simultaneously hydrogen. The compounds possess antiphlogistic, analgesic, anticonvulsive, or tranquilizing properties.

13 Claims, No Drawings

NOVEL DIHYDRO-AS-TRIAZINO[5,6-c]QUINOLINE DERIVATIVES AND A PROCESS FOR THE PREPARATION THEREOF

This invention relates to novel dihydro-as-triazino[5,6-c]quinoline derivatives, their preparation and compositions containing them.

More particularly, the invention relates to novel dihydro-as-triazino[5,6-c]quinoline compounds of the formula I

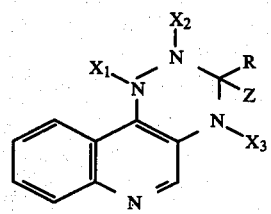

wherein
R is hydrogen, $C_{1-12}$ alkyl, an aralkyl having 1 to 4 carbon atoms in the alkyl chain and wherein the aryl group can be substituted by one or more substituents; or a phenyl group which can be substituted by one or more substituents,
$X_1$ is hydrogen, $C_{1-6}$ alkanoyl or $C_{1-6}$ haloalkanoyl,
$X_2$ and $X_3$ represent, independently, hydrogen, $C_{1-6}$ alkanoyl or $C_{1-6}$ haloalkanoyl, but one of them forms a chemical bond with Z,
but when $X_1$ is hydrogen, then one of $X_2$ and $X_3$ not forming a chemical bond with Z is other than hydrogen, and pharmaceutically acceptable acid addition salts thereof.

The novel compounds possess primarily antiphlogistic, analgesic, anticonvulsive and tranquillizing effects.

1,2-Dihydro-3-substituted-as-triazino[5,6-c]quinoline compounds are known from GB Patent Specification Nos. 1,382,781 and 1,401,164. However, as-triazino[5,6-c]quinolines substituted in positions 1, 2 and 4, respectively, have not been described previously.

In the formula I $C_{1-12}$ alkyl means a linear or branched-chain alkyl group, such as a methyl, ethyl, n-propyl, isopropyl, n-butyl, sec.-butyl, tert.-butyl, isobutyl, pentyl, hexyl, heptyl, octyl, nonyl, decyl, undecyl or dodecyl group.

An aralkyl group having 1 to 4 carbon atoms in the alkyl chain is preferably a benzyl, phenylethyl or naphthylmethyl group.

An aryl or phenyl group can be substituted by one or more, preferably 1 to 3 identical or different substituents, such as halogen, $C_{1-4}$ alkyl and $C_{1-4}$ alkoxy.

The $C_{1-6}$ alkanoyl group means a linear or branched-chain alkanoyl group, such as a formyl, acetyl, propionyl, butyryl, isobutyryl, valeryl or hexanoyl group.

A $C_{1-6}$ haloalkanoyl group is a halogenated, preferably fluorinated, chlorinated or brominated, alkanoyl group, such as a trichloroacetyl, trifluoroacetyl, 2-chloroacetyl, 2-fluoroacetyl, 2-bromoacetyl, 2,2-difluoroacetyl or 2,2-dichloroacetyl group.

The pharmaceutically acceptable acid addition salt can be an inorganic acid addition salt, such as sulfate, hydrochloride, hydrobromide, etc. or an organic acid addition salt, such as acetate, oxalate, tartrate, maleinate, fumarate, etc.

A subclass of the compounds of the invention consists of the 1,4-dihydro-as-triazino[5,6-c]quinoline derivatives of the formula Ia

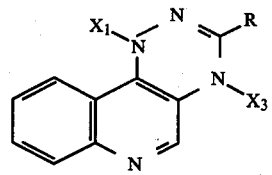

wherein R and $X_1$ are as stated above, $X_3$ is $C_{1-6}$ alkanoyl or $C_{1-6}$ haloalkanoyl, and the pharmaceutically acceptable acid addition salts thereof.

Preferably, $X_1$ and $X_3$ represent, independently, $C_{1-6}$ alkanoyl or $C_{1-6}$ haloalkanoyl.

A further subclass of the compounds of the invention consists of the 1,2-dihydro-as-triazino[5,6-c]quinoline derivatives of the formula Ib

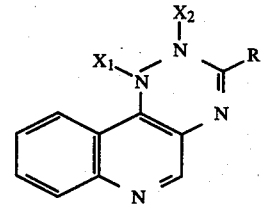

wherein R is as stated above, $X_1$ is $C_{1-6}$ alkanoyl or $C_{1-6}$ haloalkanoyl, $X_2$ is hydrogen atom, $C_{1-6}$ alkanoyl or $C_{1-6}$ haloalkanoyl, and the pharmaceutically acceptable acid addition salts thereof.

Preferred dihydro-as-triazino[5,6-c]quinoline derivatives of the invention are as follows:
1-acetyl-3-amyl-1,2-dihydro-as-triazino[5,6-c]quinoline,
4-acetyl-3-phenyl-1,4-dihydro-as-triazino[5,6-c]quinoline,
1-acetyl-3-butyl-1,2-dihydro-as-triazino[5,6-c]quinoline,
1-acetyl-3-octyl-1,2-dihydro-as-triazino[5,6-c]quinoline,
1-acetyl-3-isobutyl-1,2-dihydro-as-triazino[5,6-c]quinoline,
1-acetyl-3-tert.-butyl-1,2-dihydro-as-triazino[5,6-c]quinoline,
1-acetyl-3-(3'-methyl-1'-butyl)-1,2-dihydro-as-triazino[5,6-c]quinoline.

The novel dihydro-as-triazino[5,6-c]quinoline derivatives of the formula I and the pharmaceutically acceptable acid addition salts thereof are prepared by reacting an acid addition salt of a dihydro-as-triazino[5,6-c]quinoline of the formula II

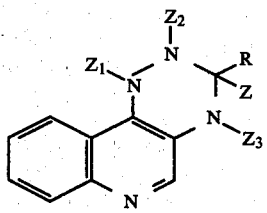

wherein R is as stated above, $Z_1$ is hydrogen, $Z_2$ and $Z_3$ are hydrogen, but one of them forms a chemical bond with Z, with an active acylating derivative of a $C_{1-6}$ alkanecarboxylic acid or a $C_{1-6}$ haloalkanecarboxylic acid and, if desired, reacting a monoacylated compound optionally liberated from its acid addition salt with an active acylating derivative of a $C_{1-6}$ alkanecarboxylic acid or a $C_{1-6}$ haloalkanecarboxylic acid to form a diacylated compound of the formula I and, if desired, converting any compound of the formula I with an inorganic or organic acid into its acid addition salt, or liberating the compound of the formula I from its acid addition salt with a base.

The acylating agent employed is preferably a carboxylic anhydride of the formula III

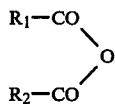

wherein $R_1$ and $R_2$ represent, independently, a hydrogen atom, a $C_{1-5}$ alkyl group or a $C_{1-5}$ haloalkyl group.

Preferably, the acylation reactions of the invention are performed in a carboxylic acid corresponding to the acylating agent used. However, an excess of the acylating agent may be used as solvent or diluent. In addition, the acylation can be performed in the presence of any inert solvent that does not react with the reaction components present.

In general, the reaction temperature is from 0° C. to 200° C., preferably from 40° to 150° C. Usually, the starting compounds of the formula II are acylated at the boiling point of the reaction mixture.

The starting substance is preferably reacted with 2 to 3 equimolar quantity of the acylating agent, usually at the boiling point of the reaction mixture. The product that precipitates on cooling consists of the acid addition salt of the monoacylated dihydro-as-triazino[5,6-c]quinoline, in general. The monoacylated product can be transformed into the diacylated compound through a further acylation step with an excess of the acylating agent as given above. In this case, the monoacylated product is preferably liberated with a base, such as sodium hydrogen carbonate from the acid addition salt prior to diacylation.

In some cases, mono- and diacylated products can simultaneously form depending on the reaction conditions, such as excess of acylating agent and reaction time.

The formation of the monoacylated dihydro-as-triazino[5,6-c]quinoline is preferred by a shorter reaction time and a lower excess of acylating agent. Diacylation can be made complete by a longer reaction time and a higher excess of acylating agent.

If desired, an obtained compound of the formula I can be liberated from the acid addition salt or transformed into a pharmaceutically acceptable acid addition salt.

The starting compounds of the formula II can be prepared as given in GB Patent Specification Nos. 1,382,781 and 1,401,164.

The novel dihydro-as-triazino[5,6-c]quinolines of the formula I have shown biological effects in several pharmacological tests. Primarily, the compounds possess antiphlogistic, analgesic, anticonvulsive and tranquillizing effects, furthermore potentiate the effects of narcotics.

The acute toxicity of the compounds of the formula I was determined on both female and male mice weighing 18 to 24 g. The compounds were administered orally. The $LD_{50}$ values obtained are summarized in Table I in which the toxicity of the following reference substances are given, too:

meprobamate [2-methyl-2-propylpropane-1,3-diol dicarbamate],
phenylbutazone [4-butyl-1,2-diphenylpyrazolidine-3,5-dione],
paracetamole [p-hydroxyacetanilide],
trimethadione [3,5,5-trimethyloxazolidine-2,4-dione] and
amitriptylin [5-(3-dimethylaminopropylidene)-10,11-dihydro-5H-dibenzo[a,d]cycloheptene].

TABLE I

| Acute toxicity | |
|---|---|
| Compound /No. of Example/ | $LD_{50}$ p.o. mg/kg |
| 1 | 2000 |
| 3 | 2000 |
| 6 | 2000 |
| 7 | 2000 |
| 8 | 2000 |
| 9 | 2000 |
| 10 | 2000 |
| meprobamate | 1100 |
| phenylbutazone | 1000 |
| paracetamole | 540 |
| trimethadione | 2050 |
| amitriptylin | 225 |

The analgesic effect was studied by means of the acetic acid writhing test on mice. After the intraperitoneal administration of 0.4 ml of 0.5 percent acetic acid, the writhing responses were counted between the fifth and tenth minutes. The writhing number was calculated as the percentage of the control value. The compounds tested were orally administered to the animals 1 hour prior to the treatment with acetic acid. The control group was treated orally with a carrier without active substance. The results obtained are summarized in Table II in which the values of $ED_{50}$ and therapeutic index of the test compounds as well as the reference substances are given. Paracetamole and phenylbutazone were used as reference substance.

TABLE II

| | Analgesic effect | |
|---|---|---|
| Compound (No. of Example) | $ED_{50}$ p.o. mg/kg | Therapeutic index $LD_{50}/ED_{50}$ |
| 1 | 125 | 16 |
| 6 | 320 | 6 |
| 10 | 100 | 20 |
| paracetamole | 180 | 3 |
| phenylbutazone | 60 | 16 |

The antiphlogistic effect of the novel compounds of the invention was investigated on rats by the method of Winter [J. Pharm. Exp. Ther., 141, 369 /1963/]. 0.1 ml of a 1 percent carrageenin suspension was injected, subcutaneously, into the plantar region of one of the hind paws. The compounds to be tested were administered orally into the animals 1 hour before the injection of the carrageenine suspension. The volume of the treated paw was measured by mercury-plethysmometer before and 3 hours after injection. The results obtained are summarized in Table III in which the values of $ED_{50}$ and therapeutic index of the test compounds as well as the reference substance (phenylbutazone) are given.

TABLE III

| Antiphlogistic effect | | |
|---|---|---|
| Compound (No. of Example) | ED$_{50}$ p.o. mg/kg | Therapeutic index LD$_{50}$/ED$_{50}$ |
| 1 | 100 | 20 |
| 6 | 36 | 55 |
| 10 | 200 | 10 |
| phenylbutazone | 100 | 10 |

The anticonvulsive effect of the novel compounds was studied on white mice weighing 20 to 25 g through the inhibition of the spasm developed by electroshock. The electroshock was provoked by means of corneal electrodes with a current intensity of 45 mA. The frequency of the current used was equivalent to 50 Hz, and the duration of each electroshock was 0.4 sec. The complete inhibition of the tonic extension of the hind limbs was taken as criterium of the anticonvulsive effect. The compounds to be tested were administered orally 1 hour prior to the electroshock. The results obtained are shown in Table IV in which the values of ED$_{50}$ and therapeutic index of the test compounds as well as the reference substance (trimethadione) are given.

TABLE IV

| Inhibition of the spasm provoked by electroshock | | |
|---|---|---|
| Compound (No. of Example) | ED$_{50}$ p.o. mg/kg | Therapeutic index LD$_{50}$/ED$_{50}$ |
| 6 | 160 | 12.5 |
| 7 | 450 | 4.4 |
| 8 | 200 | 10 |
| trimethadione | 400 | 5.3 |

The anticonvulsive effect of the compounds was also studied through the inhibition of the spasm provoked by pentamethylenetetrazole [6,7,8,9-tetrahydro-5H-tetrazoloazepine]. 125 mg/kg doses of pentamethylenetetrazole were administered intraperitoneally into white mice divided into groups consisting of 6 animals and the tonic extension spasms of the hind limbs were registered. The compounds to be tested were administered orally 1 hour before the injection of pentamethylenetetrazole. The results obtained are summarized in Table V in which the values of ED$_{50}$ and therapeutic index of the test compounds as well as the reference substance (trimethadione) are given.

TABLE V

| Inhibition of spasms provoked by pentamethylenetetrazole | | |
|---|---|---|
| Compound (No. of Example) | ED$_{50}$ p.o. mg/kg | Therapeutic index LD$_{50}$/ED$_{50}$ |
| 6 | 90 | 22,2 |
| 7 | 350 | 5,7 |
| 8 | 72 | 27,8 |
| 9 | 165 | 12 |
| trimethadione | 490 | 4,3 |

The narcosis potentiating effect of the novel compounds of the formula I was tested on groups consisting of 6 mice each. The animals belonging to the control group received an oral dosage of 20 ml/kg of 0.9 percent aqueous sodium chloride solution, whereas the other animals were treated orally with the compound to be tested. After 1 hour, 40 mg/kg of hexobarbital [5-(1-cyclohexenyl-1,5-dimethylbarbituric acid] were administered intravenously into the animals. A 150 percent prolongation of the sleeping time, related to the average value observed in the controls, was regarded as positive response. The number of animals giving positive response was compared to the total number of the animals treated. The ED$_{50}$ values calculated from these data as well as the therapeutical indices are listed in Table VI. Meprobamate was employed as reference substance.

TABLE VI

| Narcosis potentiating effect | | |
|---|---|---|
| Compound (No. of Example) | ED$_{50}$ p.o. mg/kg | Therapeutic index LD$_{50}$/ED$_{50}$ |
| 1 | 200 | 10 |
| 3 | 150 | 13.3 |
| 6 | 125 | 16 |
| 8 | 70 | 28.5 |
| 10 | 100 | 20 |
| meprobamate | 260 | 4.2 |

The tetrabenazine antagonizing effect of the novel compounds was tested on groups consisting of 10 mice each. The animals belonging to the control group received an oral dosage of 20 ml/kg of 0.9 percent aqueous sodium chloride solution, whereas the other animals were treated orally with the compound to be tested. 30 minutes after the introduction of the active agent or the vehicle, 50 mg/kg of tetrabenazine [3-isobutyl-9,10-dimethoxy-1,2,3,4,6,7-hexahydrobenzo[a]quinolizine-2-one] were administered intraperitoneally. The animals with closed palpebral fissures were counted 30, 60, 90 and 120 minutes after the administration of tetrabenazine. The data obtained in the individual measuring times were added, and the percentage inhibition related to the controls was calculated. The ED$_{50}$ values and the therapeutical indices calculated therefrom are listed in Table VII. Amitriptylin was employed as reference compound.

TABLE VII

| Tetrabenazine antagonism | | |
|---|---|---|
| Compound (No. of Example) | ED$_{50}$ p.o. mg/kg | Therapeutic index LD$_{50}$/ED$_{50}$ |
| 8 | 20 | 100 |
| 10 | 14.5 | 138 |
| 11 | 54 | 37 |
| amitriptylin | 12 | 19 |

The dihydro-as-triazino[5,6-c]quinolines of the formula I as well as the acid addition salts thereof can be employed as active substances in pharmaceutical compositions. The pharmaceutical products are prepared by admixing the novel compounds of the formula I or their acid addition salts with one or more solid or liquid pharmaceutical carriers and transforming the mixture obtained into pharmaceutical products.

A typical dose for adult patients is 1 to 1000 mg/kg, especially 5 to 500 mg/kg.

Preferably pharmaceutical products for oral administration, such as tablets, capsules, coated tablets, solutions, suspensions, etc. or for parenteral administration, such as sterile solutions or suspensions, are prepared.

Carriers in the solid pharmaceutical products may be binding agents, such as gelatin, sorbitol, polyvinylpyrrolidone, filling agents, such as lactose, sugar, starch, calcium phosphate, auxiliary agents for tabletting, such as magnesium stearate, polyethyleneglycol, silica, wetting agents, such as sodium laurylsulfate, etc.

Carriers in the liquid pharmaceutical products may be suspending agents, such as sorbitol, sugar solution, gelatine carboxymethylcellulose, emulsifying agents, such as sorbitan monooleate, solvents, such as oils, glycine, propyleneglycol, ethanol, preservatives, such as methyl p-hydroxybenzoate, propyl p-hydroxybenzoate, etc.

If desired, the pharmaceutical products may contain known flavoring and coloring agents, too.

Further details of the invention are illustrated by the following non-limiting Examples.

EXAMPLE 1

1-Acetyl-3-amyl-1,2-dihydro-as-triazino[5,6c]quinoline 13.0 g (0.045 moles) of 3-amyl-1,2-dihydro-as-triazino[5,6-c]quinoline hydrochloride were heated with 30 ml of acetic anhydride for 15 minutes under reflux. After 5 minutes, boiling the starting compound was dissolved and after another 5 minutes the product began to precipitate as paprika-red crystals. After cooling the crystals were filtered and washed with ethyl acetate. Thus, 11.2 g (74.8%) of 1-acetyl-3-amyl-1,2-dihydro-as-triazino[5,6-c]quinoline hydrochloride were obtained, m.p.: 212°–213° C.

6.0 g [0.018 moles] of 1-acetyl-3-amyl-1,2-dihydro-as-triazino[5,6-c]quinoline hydrochloride were suspended in 40 ml of water and the suspension was adjusted with a concentrated sodium bicarbonate solution to pH 7. The yellow crystals obtained were filtered and washed with water.

Thus, 5.26 g (98.5%) of 1-acetyl-3-amyl-1,2-dihydro-as-triazino[5,6-c]quinoline were obtained, m.p.: 178°–180° C.

EXAMPLE 2

1,2-Diacetyl-3-amyl-1,2-dihydro-as-triazino[5,6-c]quinoline 9.5 g (0.032 moles) of 1-acetyl-3-amyl-1,2-dihydro-as-triazino[5,6-c]quinoline were boiled with 85 ml of acetic anhydride for 4 hours and the solution was poured into water. The pale yellow crystals obtained were filtered and washed with water. Thus, 9.25 g (85.3%) of 1,2-diacetyl-3-amyl-1,2-dihydro-as-triazino[5,6-c]quinoline were obtained, m.p.: 116°–117° C.

EXAMPLE 3

4-Acetyl-3-phenyl-1,4-dihydro-as-triazino[5,6-c]quinoline 10.0 g (0.033 moles) of 3-phenyl-1,4-dihydro-as-triazino[5,6-c]quinoline hydrochloride were boiled with 20 ml of acetic anhydride for 1 hour. The dark violet color of the starting compound disappeared during the reaction and the product precipitated as brick colored crystals.

Thus, 6.2 g (55.6%) of 4-acetyl-3-phenyl-1,4-dihydro-as-triazino[5,6-c]quinoline hydrochloride were obtained, m.p.: 256°–258° C.

6.2 g (0.018 moles) of 4-acetyl-3-phenyl-1,4-dihydro-as-triazino[5,6-c]quinoline hydrochloride were suspended in 100 ml of water and the suspension was adjusted with a concentrated sodium bicarbonate solution to pH 7. The yellow crystals obtained were filtered and washed with water.

Thus, 5.0 g (92%) of 4-acetyl-3-phenyl-1,4-dihydro-as-triazino[5,6-c]quinoline were obtained, m.p.: 267°–268° C.

EXAMPLE 4

1,4-Diacetyl-3-phenyl-1,4-dihydro-as-triazino[5,6-c]quinoline 10.0 g (0.033 moles) of 3-phenyl-1,4-dihydro-as-triazino[5,6-c]quinoline hydrochloride were boiled with 50 ml of acetic anhydride for 3 hours. The solution obtained was poured into water and the crystals precipitated were filtered and washed with water.

Thus, 7.0 g (68%) of 1,4-diacetyl-3-phenyl-1,4-dihydro-as-triazino[5,6-c]quinoline were obtained, m.p.: 200°–202° C.

The same compound can be obtained by reacting 4-acetyl-3-phenyl-1,4-dihydro-as-triazino[5,6-c]quinoline prepared as described in Example 3 or the acid addition salt thereof with acetic anhydride.

EXAMPLE 5

1-Propionyl-2-acetyl-3-amyl-1,2-dihydro-as-triazino[5,6-c]quinoline 3.5 g (0.01 moles) of 1-propionyl-3-amyl-1,2-dihydro-as-triazino[5,6-c]quinoline were boiled with 30 ml of acetic anhydride for 3 hours. The mixture was poured into water, the product solidified was filtered and washed with water.

Thus, 2.4 g (68%) of 1-propionyl-2-acetyl-3-amyl-1,2-dihydro-as-triazino[5,6-c]quinoline were obtained, m.p.: 115°–116° C.

EXAMPLE 6

1-Acetyl-3-butyl-1,2-dihydro-as-triazino[5,6-c]quinoline

3-Butyl-1,2-dihydro-as-triazino[5,6-c]quinoline hydrochloride was acylated with acetic anhydride as described in Example 1 to obtain 1-acetyl-3-butyl-1,2-dihydro-as-triazino[5,6-c]quinoline with a yield of 61%. M.p.: 168°–170° C. The hydrochloride melts at 218°–220° C.

EXAMPLE 7

1-Acetyl-3-octyl-1,2-dihydro-as-triazino[5,6-c]quinoline

3-Octyl-1,2-dihydro-as-triazino[5,6-c]quinoline hydrochloride was acylated with acetic anhydride as described in Example 1 to obtain 1-acetyl-3-octyl-1,2-dihydro-as-triazino[5,6-c]quinoline with a yield of 63%. M.p.: 97°–99° C. The hydrochloride melts at 210°–212° C.

EXAMPLE 8

1-Acetyl-3-isobutyl-1,2-dihydro-as-triazino[5,6-c]quinoline

3-Isobutyl-1,2-dihydro-as-triazino[5,6-c]quinoline hydrochloride was acylated with acetic anhydride as described in Example 1 to obtain 1-acetyl-3-isobutyl-1,2-dihydro-as-triazino[5,6-c]quinoline with a yield of 65%. M.p.: 234°–236° C. The hydrochloride melts at 206°–208° C.

EXAMPLE 9

1-Acetyl-3-tert.-butyl-1,2-dihydro-as-triazino[5,6-c]quinoline 3-tert.-Butyl-1,2-dihydro-as-triazino[5,6-c]quinoline hydrochloride was acylated with acetic anhydride as described in Example 1 to obtain 1-acetyl-3-tert.-butyl- 1,2-dihydro-as-triazino[5,6-c]quinoline with a yield of 71%. M.p.: 272°–274° C. The hydrochloride melts at 268°–270° C.

EXAMPLE 10

1-Acetyl-3-(3'-methyl-1'-butyl)-1,2-dihydro-as-triazino[5,6-c]quinoline 3-(3'-Methyl-1'-butyl)-1,2-dihydro-as-triazino[5,6-c]quinoline hydrochloride was acylated with acetic anhydride as described in Example 1 to obtain 1-acetyl-3-(3'-methyl-1'-butyl)-1,2-dihydro-as-triazino[5,6-c]quinoline with a yield of 52%. M.p.: 124°–126° C. The hydrochloride melts at 194°–196° C.

EXAMPLE 11

1-Acetyl-3-[1'-ethyl-1'-propyl]-1,2-dihydro-as-triazino[5,6-c]quinoline 3-(1'-Ethyl-1'-propyl)-1,2-dihydro-as-triazino[5,6-c]quinoline hydrochloride was acylated with acetic anhydride as described in Example 1 to obtain 1-acetyl-3-(1'-ethyl-1'-propyl)-1,2-dihydro-as-triazino[5,6-c]quinoline with a yield of 75%. M.p.: 245°–247° C. The hydrochloride melts at 212°–214° C.

EXAMPLE 12

1-Acetyl-3-(2',2'-dimethylpropyl)-1,2-dihydro-as-triazino[5,6-c]quinoline 3-(2',2'-Dimethylpropyl)-1,2-dihydro-as-triazino[5,6-c]quinoline hydrochloride was acylated with acetic anhydride as described in Example 1 to obtain 1-acetyl-3-(2',2'-dimethylpropyl)-1,2-dihydro-as-triazino[5,6-c]quinoline with a yield of 45%. M.p.: 248°–250° C. The hydrochloride melts at 235°–237° C.

EXAMPLE 13

1-Acetyl-3-benzyl-1,2-dihydro-as-triazino[5,6-c]quinoline

3-Benzyl-1,2-dihydro-as-triazino[5,6-c]quinoline hydrochloride was acylated with acetic anhydride as described in Example 1 to obtain 1-acetyl-3-benzyl-1,2-dihydro-as-triazino[5,6-c]quinoline with a yield of 63%. M.p.: 195°–197° C. The hydrochloride melts at 215°–216° C.

EXAMPLE 14

1-Acetyl-3-(beta-phenylethyl)-1,2-dihydro-as-triazino[5,6-c]quinoline 3-(beta-Phenylethyl)-1,2-dihydro-as-triazino[5,6-c]quinoline hydrochloride was acylated with acetic anhydride as described in Example 1 to obtain 1-acetyl-3-(beta-phenylethyl)-1,2-dihydro-as-triazino[5,6-c]quinoline with a yield of 35%. M.p.: 238°–240° C. The hydrochloride melts at 206°–208° C.

EXAMPLE 15

1-Acetyl-3-(3',4'-dimethoxybenzyl)-1,2-dihydro-as-triazino[5,6-c]quinoline 3-(3',4'-Dimethoxybenzyl)-1,2-dihydro-as-triazino[5,6-c]quinoline hydrochloride was acylated with acetic anhydride as described in Example 1 to obtain 1-acetyl-3-(3',4'-dimethoxybenzyl)-1,2-dihydro-as-triazino[5,6-c]quinoline with a yield of 54%. M.p.: 200°–202° C. The hydrochloride melts at 235°–236° C.

EXAMPLE 16

1-Propionyl-3-amyl-1,2-dihydro-as-triazino[5,6-c]quinoline hydrochloride

3-Amyl-1,2-dihydro-as-triazino[5,6-c]quinoline hydrochloride was acylated with propionyl anhydride as described in Example 1 to obtain 1-propionyl-3-amyl-1,2-dihydro-as-triazino[5,6-c]quinoline hydrochloride, m.p.: 236°–238° C.

EXAMPLE 17

1-Butyryl-3-amyl-1,2-dihydro-as-triazino[5,6-c]quinoline

3-Amyl-1,2-dihydro-as-triazino[5,6-c]quinoline hydrochloride was acylated with butyryl anhydride as described in Example 1 to obtain 1-butyryl-3-amyl-1,2-dihydro-as-triazino[5,6-c]quinoline with a yield of 73%. M.p.: 123°–125° C. The hydrochloride melts at 220°–222° C.

EXAMPLE 18

1-Valeroyl-3-amyl-1,2-dihydro-as-triazino[5,6-c]quinoline

3-Amyl-1,2-dihydro-as-triazino[5,6-c]quinoline hydrochloride was acylated with valeroyl anhydride as described in Example 1 to obtain 1-valeroyl-3-amyl-1,2-dihydro-as-triazino[5,6-c]quinoline with a yield of 81%. M.p.: 118°–120° C. The hydrochloride melts at 216°–218° C.

EXAMPLE 19

1-Trifluoroacetyl-3-amyl-1,2-dihydro-as-triazino[5,6-c]quinoline

3-Amyl-1,2-dihydro-as-triazino[5,6-c]quinoline hydrochloride was acylated with trifluoroacetyl anhydride as described in Example 1 to obtain 1-trifluoroacetyl-3-amyl-1,2-dihydro-as-triazino[5,6-c]quinoline with a yield of 73%. M.p.: 187°–189° C. The hydrochloride melts at 160°–161° C.

EXAMPLE 20

1,2-Diacetyl-3-butyl-1,2-dihydro-as-triazino[5,6-c]quinoline

1-Acetyl-3-butyl-1,2-dihydro-as-triazino[5,6-c]quinoline was acylated with acetic anhydride as described in Example 2 to obtain 1,2-diacetyl-3-butyl-1,2-dihydro-as-triazino[5,6-c]quinoline with a yield of 95%. M.p.: 104°–106° C.

EXAMPLE 21

1,2-Diacetyl-3-octyl-1,2-dihydro-as-triazino[5,6-c]quinoline

1-Acetyl-3-octyl-1,2-dihydro-as-triazino[5,6-c]quinoline was acylated with acetic anhydride as described in Example 2 to obtain 1,2-diacetyl-3-octyl-1,2-dihydro-as-triazino[5,6-c]quinoline with a yield of 80%. M.P.: 95°–97° C.

EXAMPLE 22

1,2-Diacetyl-3-(3'-methyl-1'-butyl)-1,2-dihydro-as-triazino[5,6-c]quinoline

1-Acetyl-3-(3'-methyl-1'-butyl)-1,2-dihydro-as-triazino[5,6-c]quinoline was acylated with acetic anhydride as described in Example 2 to obtain 1,2-diacetyl-3-

(3'-methyl-1'-butyl)-1,2-dihydro-as-triazino[5,6-c]quinoline with a yield of 60%. M.p.: 116°–118° C.

EXAMPLE 23

1,2-Diacetyl-3-isobutyl-1,2-dihydro-as-triazino[5,6-c]quinoline

1-Acetyl-3-isobutyl-1,2-dihydro-as-triazino[5,6-c]quinoline was acylated with acetic anhydride as described in Example 2 to obtain 1,2-diacetyl-3-isobutyl-1,2-dihydro-as-triazino[5,6-c]quinoline with a yield of 58%, M.p.: 184°–186° C.

EXAMPLE 24

1,2-Diacetyl-3-(1'-ethyl-1'-propyl)-1,2-dihydro-as-triazino[5,6-c]quinoline

1-Acetyl-3-(1'-ethyl-1'-propyl)-1,2-dihydro-as-triazino[5,6-c]quinoline was acylated with acetic anhydride as described in Example 2 to obtain 1,2-diacetyl-3-(1'-ethyl-1'-propyl)-1,2-dihydro-as-triazino[5,6-c]quinoline with a yield of 67%. M.p.: 124°–126° C.

EXAMPLE 25

1,2-Diacetyl-3-benzyl-1,2-dihydro-as-triazino[5,6-c]quinoline

1-Acetyl-3-benzyl-1,2-dihydro-as-triazino[5,6-c]quinoline was acylated with acetic anhydride as described in Example 2 to obtain 1,2-diacetyl-3-benzyl-1,2-dihydro-as-triazino[5,6-c]quinoline with a yield of 62%. M.p.: 125°–127° C.

EXAMPLE 26

1,2-Diacetyl-3-(beta-phenylethyl)-1,2-dihydro-as-triazino[5,6-c]quinoline

1-Acetyl-3-(beta-phenylethyl)-1,2-dihydro-as-triazino[5,6-c]quinoline was acylated with acetic anhydride as described in Example 2 to obtain 1,2-diacetyl-3-(beta-phenylethyl)-1,2-dihydro-as-triazino[5,6-c]quinoline with a yield of 68%. M.p.: 203°–205° C.

EXAMPLE 27

1,2-Diacetyl-3-(3',4'-dimethoxybenzyl)-1,2-dihydro-as-triazino[5,6-c]quinoline

1-Acetyl-3-(3',4'-dimethoxybenzyl)-1,2-dihydro-as-triazino[5,6-c]quinoline was acylated with acetic anhydride as described in Example 2 to obtain 1,2-diacetyl-3-(3',4'-dimethoxybenzyl)-1,2-dihydro-as-triazino[5,6-c]quinoline with a yield of 98%. M.p.: 196°–197° C.

EXAMPLE 28

4-Acetyl-3-(p-tolyl)-1,4-dihydro-as-triazino[5,6-c]quinoline 3-(p-Tolyl)-1,4-dihydro-as-triazino[5,6-c]quinoline hydrochloride was acylated with acetic anhydride as described in Example 3 to obtain 4-acetyl-3-(p-tolyl)-1,4-dihydro-as-triazino[5,6-c]quinoline with a yield of 66%. M.p.: 280°–282° C. The hydrochloride melts at 254°–256° C.

EXAMPLE 29

4-Acetyl-3-(p-methoxyphenyl)-1,4-dihydro-as-triazino[5,6-c]quinoline 3-(p-Methoxyphenyl)-1,4-dihydro-as-triazino[5,6-c]quinoline hydrochloride was acylated with acetic anhydride as described in Example 3 to obtain 4-acetyl-3-(p-methoxyphenyl)-1,4-dihydro-as-triazino[5,6-c]quinoline with a yield of 10%. M.p.: 240°–241° C.

EXAMPLE 30

4-Propionyl-3-phenyl-1,4-dihydro-as-triazino[5,6-c]quinoline

3-Phenyl-1,4-dihydro-as-triazino[5,6-c]quinoline hydrochloride was acylated with propionyl anhydride as described in Example 3 to obtain 4-propionyl-3-phenyl-1,4-dihydro-as-triazino[5,6-c]quinoline with a yield of 5%. M.p.: 236°–238° C.

EXAMPLE 31

1,4-Diacetyl-3-1,4-dihydro-as-triazino[5,6-c]quinoline 3-(p-Tolyl)-1,4-dihydro-as-triazino[5,6-c]quinoline hydrochloride was acylated with acetic anhydride as described in Example 4 to obtain 1,4-diacetyl-3-(p-tolyl)-1,4-dihydro-as-triazino[5,6-c]quinoline with a yield of 77%. M.p.: 204°–205° C.

EXAMPLE 32

1,4-Diacetyl-3-(p-methoxyphenyl)-1,4-dihydro-as-triazino[5,6-c]quinoline 3-(p-Methoxyphenyl)-1,4-dihydro-as-triazino[5,6-c]quinoline hydrochloride was acylated with acetic anhydride as described in Example 4 to obtain 1,4-diacetyl-3-(p-methoxyphenyl)-1,4-dihydro-as-triazino[5,6-c]quinoline with a yield of 80%. M.p.: 193°–194° C.

EXAMPLE 33

1,4-Diacetyl-3-(3',4',5'-trimethoxyphenyl)-1,4-dihydro-as-triazino[5,6-c]quinoline 3-(3',4',5'-trimethoxyphenyl)-1,4-dihydro-as-triazino[5,6-c]quinoline hydrochloride was acylated with acetic anhydride as described in Example 4 to obtain 1,4-diacetyl-3-(3',4',5'-trimethoxyphenyl)-1,4-dihydro-as-triazino[5,6-c]quinoline with a yield of 60%. M.p.: 222°–223° C.

EXAMPLE 34

1,4-Dipropionyl-3-phenyl-1,4-dihydro-as-triazino[5,6-c]quinoline

3-Phenyl-1,4-dihydro-as-triazino[5,6-c]quinoline hydrochloride was acylated with propionyl anhydride as described in Example 4 to obtain 1,4-dipropionyl-3-phenyl-1,4-dihydro-as-triazino[5,6-c]quinoline with a yield of 46%. M.p.: 156°–157° C.

What we claim is:

1. A compound of the formula

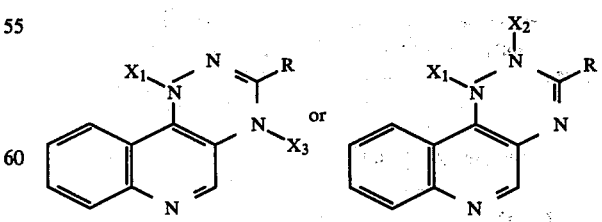

or a pharmaceutically effective salt thereof, wherein R is $C_{1-12}$ alkyl; or is phenyl or phenyl-$C_1$–$C_4$ alkyl wherein the phenyl can be substituted with 1 to 3 $C_{1-4}$ alkyl or $C_{1-4}$ alkoxy substituents; $X_1$ is hydrogen, $C_{1-6}$ alkanoyl or $C_{1-6}$ haloalkanoyl; $X_2$ and $X_3$ are hydrogen or $C_{1-6}$ alkanoyl; and when $X_1$ is hydrogen, $X_2$ and $X_3$ are not simultaneously hydrogen.

2. 1-Acetyl-3-amyl-1,2-dihydro-as-triazino[5,6-c]quinoline as defined in claim 1.

3. 4-Acetyl-3-phenyl-1,4-dihydro-as-triazino[5,6-c]quinoline as defined in claim 1.

4. 1-Acetyl-3-butyl-1,2-dihydro-as-triazino[5,6-c]quinoline as defined in claim 1.

5. 1-Acetyl-3-octyl-1,2-dihydro-as-triazino[5,6-c]quinoline as defined in claim 1.

6. 1-Acetyl-3-isobutyl-1,2-dihydro-as-triazino[5,6-c]quinoline as defined in claim 1.

7. 1-Acetyl-3-tert.-butyl-1,2-dihydro-as-triazino[5,6-c]quinoline as defined in claim 1.

8. 1-Acetyl-3-(3'-methyl-1'-butyl)-1,2-dihydro-as-triazino[5,6-c]quinoline as defined in claim 1.

9. An antiphlogistic, analgesic, anticonvulsive or tranquillizing method of treatment which comprises administering to a patient susceptible to such treatment an effective amount of a compound as defined in claim 1.

10. A pharmaceutical composition comprising an effective amount of a compound as defined in claim 1 in a pharmaceutically effective carrier.

11. A compound of the formula (Ia)

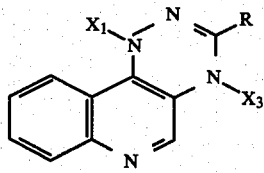

wherein

R is $C_{1-12}$ alkyl or is phenyl or phenyl-$C_{1-4}$ alkyl wherein the phenyl may be substituted with 1 to 3 $C_1$ to $C_4$ alkyl or $C_1$ to $C_4$ alkoxy substituents;

$X_1$ is hydrogen, $C_1$ to $C_6$ alkanoyl or $C_1$ to $C_6$ haloalkanoyl; and $X_3$ is $C_1$ to $C_6$ alkanoyl, or a pharmaceutically acceptable acid addition salt thereof.

12. A compound of the formula (Ib)

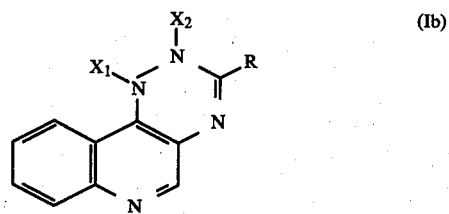

wherein

R is $C_{1-12}$ alkyl or is phenyl or phenyl-$C_1$ to $C_4$ alkyl where the phenyl may be substituted with 1 to 3 $C_1$ to $C_4$ alkyl or $C_1$ to $C_4$ alkoxy substituents;

$X_1$ is $C_1$ to $C_6$ alkanoyl or $C_1$ to $C_6$ haloalkanoyl; and $X_2$ is hydrogen or $C_1$ to $C_6$ alkanoyl, or a pharmaceutically acceptable acid addition salt thereof.

13. A compound of the formula

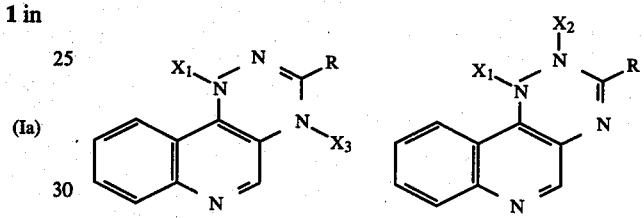

or a pharmaceutically effective salt thereof, wherein

R is hydrogen, $C_{1-12}$ alkyl; or is phenyl or phenyl-$C_1$ to $C_4$ alkyl wherein the phenyl can be substituted with 1 to 3 halogen, $C_1$ to $C_4$ alkyl, or $C_1$ to $C_4$ alkoxy substituents; and $X_1$, $X_2$ and $X_3$ are hydrogen, $C_1$ to $C_6$ alkanoyl, or $C_1$ to $C_6$ haloalkanoyl; and where $X_1$ is hydrogen, $X_2$ and $X_3$ are not simultaneously hydrogen.

* * * * *

UNITED STATES PATENT AND TRADEMARK OFFICE
CERTIFICATE OF CORRECTION

PATENT NO. : 4 342 766

DATED : 3 August 1982

INVENTOR(S) : Edit Berényi née Poldermann et al

It is certified that error appears in the above-identified patent and that said Letters Patent is hereby corrected as shown below:

On the title page, left column, item [75], the fifth inventor's name should read:

-- Ágnes Kovács née Palotay --.

Signed and Sealed this

Fourteenth Day of June 1983

[SEAL]

Attest:

DONALD J. QUIGG

Attesting Officer

Acting Commissioner of Patents and Trademarks